United States Patent
Snook et al.

(10) Patent No.: US 10,515,452 B2
(45) Date of Patent: Dec. 24, 2019

(54) SYSTEM FOR MONITORING LESION SIZE TRENDS AND METHODS OF OPERATION THEREOF

(71) Applicant: KONINKLIJKE PHILIPS N.V., Eindhoven (NL)

(72) Inventors: Allen David Snook, Snohomish, WA (US); Michael R. Vion, La Chaussee St. Victor (FR); Julia Dmitrieva, Bothell, WA (US); Junzheng Man, Bothell, WA (US)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 16/170,194

(22) Filed: Oct. 25, 2018

(65) Prior Publication Data

US 2019/0066298 A1 Feb. 28, 2019

Related U.S. Application Data (63) Continuation of application No. 15/116,266, filed as application No. PCT/IB2015/050862 on Feb. 5, 2015, now Pat. No. 10,140,714.

(Continued)

(51) Int. Cl.
*G06T 7/00* (2017.01)
*B60R 1/00* (2006.01)
(Continued)

(52) U.S. Cl.
CPC ............ *G06T 7/0016* (2013.01); *A61B 8/06* (2013.01); *A61B 8/085* (2013.01); *A61B 8/488* (2013.01);
(Continued)

(58) Field of Classification Search
CPC .......... A61B 8/06; A61B 8/085; A61B 8/488; A61B 8/5223; A61B 8/0858;
(Continued)

(56) References Cited

U.S. PATENT DOCUMENTS

| 5,782,762 A | * | 7/1998 | Vining | ................. | G06T 7/0012 |
| | | | | | 128/920 |
| 5,920,319 A | * | 7/1999 | Vining | ................ | A61B 5/1076 |
| | | | | | 345/420 |

(Continued)

FOREIGN PATENT DOCUMENTS

| WO | 0169282 A2 | 9/2001 |
| WO | 0214888 A2 | 2/2002 |

(Continued)

OTHER PUBLICATIONS

The MathWorks, Inc."Create one or more filled polygons—MATLAB patch", https://www.mathworks.com/help/matlab/ref/patch.html, 1994-2019, pp. 21 (Year: 1994).*

(Continued)

*Primary Examiner* — Mekonen T Bekele (57) ABSTRACT

A medical imaging system configured to receive first image information corresponding with one or more images acquired at a first time, the one or more images including a lesion; receive second image information corresponding with one or more images of the lesion acquired at another time; render volumes of the lesion for each image; and overlays the two volumes. Other factors and/or indicators, such as vascularization indicators, may be calculated and compared between the first image information and second image information.

10 Claims, 6 Drawing Sheets

Related U.S. Application Data (60) Provisional application No. 61/983,713, filed on Apr. 24, 2014.

(51) Int. Cl.

| | | |
|---|---|---|
| *H01Q 1/22* | (2006.01) | |
| *H01Q 1/32* | (2006.01) | |
| *H01Q 1/42* | (2006.01) | |
| *B60R 11/04* | (2006.01) | |
| *H01Q 1/12* | (2006.01) | |
| *A61B 8/06* | (2006.01) | |
| *A61B 8/08* | (2006.01) | |
| *G06T 15/08* | (2011.01) | |
| *G06T 19/00* | (2011.01) | |
| *H04N 7/18* | (2006.01) | |
| *B60R 11/00* | (2006.01) | |

(52) U.S. Cl.
CPC .............. *A61B 8/5223* (2013.01); *B60R 1/00* (2013.01); *B60R 11/04* (2013.01); *G06T 15/08* (2013.01); *G06T 19/00* (2013.01); *H01Q 1/1214* (2013.01); *H01Q 1/22* (2013.01); *H01Q 1/3275* (2013.01); *H01Q 1/42* (2013.01); *A61B 8/0858* (2013.01); *A61B 8/0891* (2013.01); *A61B 8/483* (2013.01); *B60R 2011/004* (2013.01); *G06T 2207/10132* (2013.01); *G06T 2207/30096* (2013.01); *G06T 2207/30101* (2013.01); *G06T 2210/41* (2013.01); *H04N 7/183* (2013.01)

(58) Field of Classification Search
CPC ..... A61B 8/0891; A61B 8/483; G06T 7/0016; G06T 2207/10132; G06T 2207/30096; G06T 2207/30101; G06T 2210/41; G06T 15/08; G06T 19/00
See application file for complete search history.

(56) References Cited

U.S. PATENT DOCUMENTS

| | | | | |
|---|---|---|---|---|
| 6,248,070 | B1* | 6/2001 | Kanda ..................... | A61B 8/06 128/916 |
| 7,289,651 | B2 | 10/2007 | Vining et al. | |
| 7,747,055 | B1* | 6/2010 | Vining ................... | A61B 6/466 382/131 |
| 8,078,262 | B2 | 12/2011 | Murphy et al. | |
| 8,260,013 | B2 | 9/2012 | Pekar et al. | |
| 8,594,401 | B2 | 11/2013 | Mori et al. | |
| 8,682,045 | B2 | 3/2014 | Vining et al. | |
| 9,014,448 | B2 | 4/2015 | Buelow et al. | |
| 9,603,668 | B2* | 3/2017 | Weingarten ............. | G06T 19/20 |
| 9,655,498 | B2* | 5/2017 | Kawasaki .......... | A61B 1/00009 |
| 9,848,953 | B2* | 12/2017 | Weingarten ............. | G06T 19/20 |
| 10,140,714 | B2* | 11/2018 | Snook ..................... | G06T 17/30 |
| 2003/0072479 | A1* | 4/2003 | Sofia Totterman ..... | G06T 17/10 382/131 |
| 2007/0049785 | A1 | 3/2007 | Pekar et al. | |
| 2009/0074264 | A1 | 3/2009 | Pekar et al. | |
| 2009/0254140 | A1* | 10/2009 | Rosenberg ........... | A61B 5/0422 607/17 |
| 2010/0265251 | A1 | 10/2010 | Vining et al. | |
| 2011/0152686 | A1 | 6/2011 | Snook et al. | |
| 2011/0254842 | A1 | 10/2011 | Dmitrieva et al. | |
| 2011/0255754 | A1 | 10/2011 | Dmitrieva et al. | |
| 2011/0268336 | A1* | 11/2011 | Dmitrieva ............. | G06T 7/0014 382/131 |
| 2012/0172724 | A1 | 7/2012 | Hill et al. | |
| 2012/0243765 | A1 | 9/2012 | Buelow et al. | |
| 2013/0079624 | A1 | 3/2013 | Rapoport | |
| 2013/0188851 | A1* | 7/2013 | Miyasa ................. | G06T 7/0012 382/131 |
| 2014/0081079 | A1 | 3/2014 | Kawasaki et al. | |
| 2014/0187908 | A1* | 7/2014 | Ellermann ........... | A61B 5/7235 600/410 |

FOREIGN PATENT DOCUMENTS

| | | | |
|---|---|---|---|
| WO | 2010018513 A2 | 2/2010 | |
| WO | 2010073178 A1 | 7/2010 | |
| WO | 2010115885 A1 | 10/2010 | |
| WO | WO-2010115885 A1 * | 10/2010 | ........... A61B 5/7435 |

OTHER PUBLICATIONS

The MathWorks, Inc"Introduction to Patch Objects—MATLAB & Simulink", https://www.mathworks.com/help/matlab/visualize/introduction-to-patch-objects.html, pp. 3 (Year: 1994).*

* cited by examiner

SYSTEM FOR MONITORING LESION SIZE TRENDS AND METHODS OF OPERATION THEREOF

CROSS-REFERENCE TO RELATED APPLICATIONS

This application is a Continuation of U.S. application Ser. No. 15/116,266, filed on Aug. 3, 2016, which is the U.S. National Phase Application under 35 U.S.C. § 371 of International Application No. PCT/IB2015/050862, filed Feb. 5, 2015, which claims the benefit of U.S. Provisional Application Ser. No. 61/983,713, filed Feb. 12, 2014, the disclosure of which is hereby incorporated by reference herein.

The present system relates generally to a medical imaging system and more particularly, to an ultrasound imaging system with an image evaluation technique, and a method of operation thereof.

An important factor in the treatment of cancer is the ability for a physician to determine the efficacy of treatment. Efficacy of a treatment may be defined by slowing or reduction in tumor growth, reducing tumor vascularization, or other biological parameters. When a physician cannot accurately determine the efficacy of treatment, a cancer patient may be needlessly subjected to ineffective treatments with detrimental side-effects that reduce quality of life. Poor efficacy determination may also cause a delay in transferring the patient to a treatment that may be more effective at treating the patient's cancer. This delay could negatively impact the patient's outcome.

Efficacy of tumor treatment is often evaluated using non-invasive imaging methods as repeated surgical investigations of the tumor site may be impractical or impossible. Imaging methods that do not require ionizing radiation, such as ultrasound imaging, may be advantageous when patients require multiple evaluations. In order for a physician to draw conclusions about tumor growth or reduction, it is advantageous to have consistent measurements from each point in time to each successive point in time when a new image is acquired. Inconsistency in measurements could be introduced by individual variation, rotations or changes in acquisition parameters for the acquired view, changes in physicians, or other factors. These inconsistencies may hinder the physician's ability to evaluate efficacy of tumor treatment.

According to one illustrative embodiment of the invention disclosed, a medical imaging system configured to receive first image information and second information, e.g., of a lesion over time, render a first volume and a second volume based on the image information, and overlay the first and second volumes. The system may be further configured to determine coordinate information corresponding to location information in the image information. The coordinate information may be based upon calculated image contour information. The image information may further include vascular information of the lesion. The controller may be configured to determine vascular indexes based on the vascular information. The vascular index of the first volume and the second volume may be compared by the controller. The vascular index may be defined as the percentage of the volume that includes blood flow. The vascular information may be derived from Doppler information. The imaging system may further comprise an ultrasound probe with which to acquire the image information.

According to another disclosed embodiment of the present invention, an image processing method may include receiving first image information at a first time and second information at a second time, the first and second image information including data corresponding to a lesion in a tissue; rendering a first volume and a second volume of the lesion from the image information; and overlaying the second volume and the first volume of the lesion, wherein the volumes can be defined by wire frames or meshes generated by an imaging system. The method may also include the act of acquiring image information from an ultrasonic probe. The image processing method may include acquiring a sequence of images over time to identify changes in lesion volume. The image processing method may include taking a ratio of the first and second volumes of a lesion, e.g., a tumor. The image processing method may further include calculating the surface area of the first and second volumes. The image processing method may then plot the surface area of the first and second volumes with respect to time, and may further calculate a rate of change of the surface area of the volumes between the first and second times. The image processing method may render a wire frame or a surface for the volumes.

According to another aspect of the present invention, there is disclosed an application embodied on a non-transitory computer readable medium configured to receive image information from an ultrasonic probe. The application may include code which causes a controller in an imaging system to receive first image information and second image information, the first and second image information including data corresponding to a lesion in a tissue; render first and second volumes from the image information of the lesion; and overlay the second volume on the first volume. Moreover, the code may cause the controller to calculate an indicator for the first and second volumes. The controller may further calculate the difference between the indicator for the first volume and the indicator for the second volume. The indicator may be the vascular index.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number, with the exception that identical components which appear in multiple figures are identified by the same reference numbers. Moreover, for the purpose of clarity, detailed descriptions of certain features will not be discussed when they would be apparent to those with skill in the art so as not to obscure the description of the present system.

In one embodiment, there is provided a system, application, and/or method for systematically performing a medical assessment of a lesion such as a solid tumor at multiple points in time, so as to standardize medical image reporting, which may reduce evaluation times and errors. Accordingly, costs for acquiring, reporting, and/or evaluating medical images may be reduced. Evaluation of treatment efficacy may also be improved.

Figure 1A:
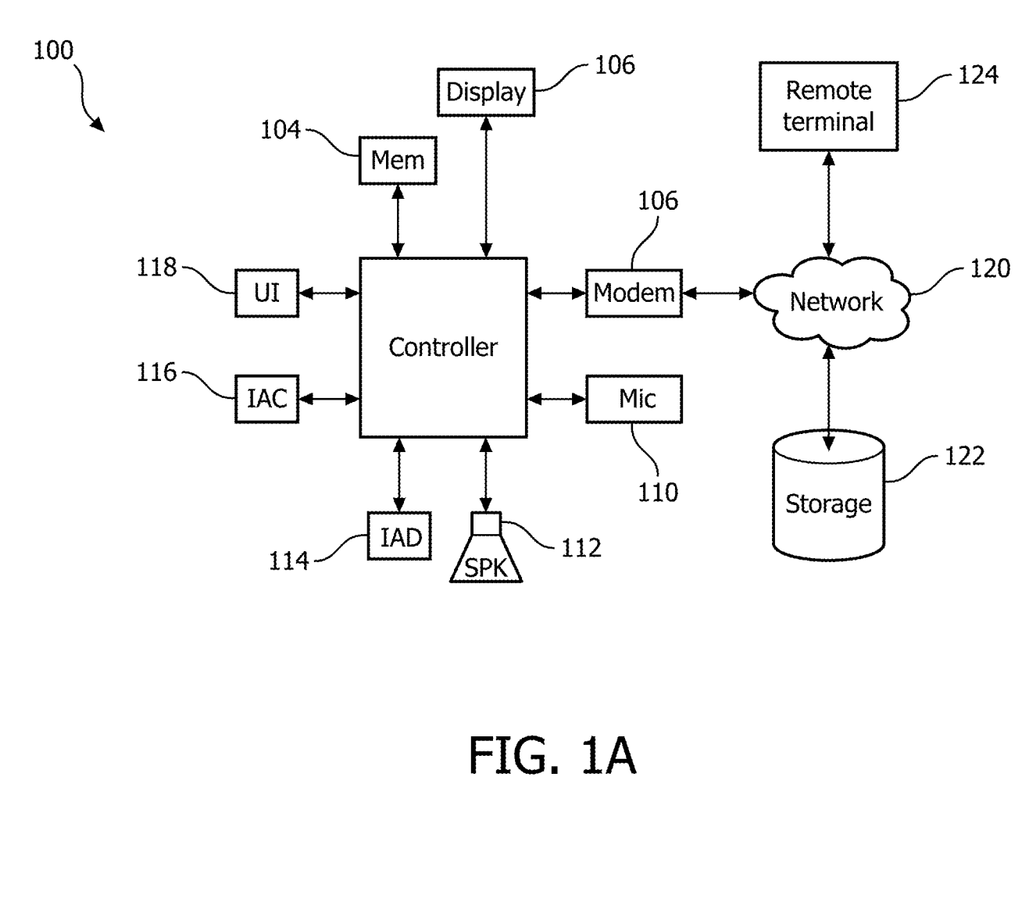
FIG. 1A is a schematic view of an embodiment of an image-capturing system according to the present system.

A schematic view of an embodiment of an image-capturing system 100 according to one embodiment of the present system is illustrated in FIG. 1A. The image-capturing system 100 may include one or more of a controller 102, a memory 104, a display 106, a modem 108, an audio input device (MIC) 110, an audio output device (SPK) 112, an image acquisition device (IAD) 114, an image acquisition control (IAC) device 116, a user interface (UI) 118, a network 120, a remote storage device 122, and a remote device or terminal 124.

The controller 102 controls or is configured to control the overall operation of the image-capturing system 100 and may include one or more controllers which may be located at the same location or at different locations. For example, one or more of the controllers may be located at the remote device 124. Accordingly, certain actions performed by one or more of the processes of the present invention may be performed at the remote device.

The memory 104 may interface with the controller 102 and may store or be configured to store programs and data which may be read and/or stored by the image-capturing system 100. The memory 104 may include one or more of a hard disc, a read-only memory (ROM), a random-access memory (RAM), a flash drive, an optical drive, and/or another suitable memory device. Further, the memory 104 may include different types of memory and may be located at a plurality of locations. The memory may include the programs and/or data created by operation of the present systems, devices, and/or methods.

The display 106 may display information under the control of one or more controllers such as, for example, the controller 102. The display 106 may include any suitable display such as, for example, cathode ray tubes (CRTs), liquid crystal displays (LCDs), plasma displays, touch screens, etc. The display 106 may include multiple displays which may be located at different locations. The display 106 may also receive user inputs.

The modem 108 may operate under the control of the controller 102 and may transmit and/or receive data to/from the controller 102 to various locations via, for example, the network 120. The modem 108 may include any suitable modem or modems and may communicate via a wired and/or a wireless link.

The audio input device 110 (MIC) may include any suitable device for inputting audio information, such as, for example, a microphone and/or transducer. The audio input device 110 may transmit received audio information to the controller 102 via, for example, a coder/decoder (CODEC). The audio input device 110 may also be located at a remote location and may transmit information via, for example, the network 120. The audio input device 110 may receive audio inputs from, for example, a user. A voice recognition program may then translate these commands for use by the controller 102. A translation program such as, for example, a speech-to-text converter, may be used to convert sound information (e.g., a user's voice, a command, etc.) into text or other data.

An audio output device 112 (SPK) may output audio information for a user's convenience. The audio output device 112 may include a speaker 112 and may output audio information received from, for example, the controller 102, via, for example, the CODEC. Further, a translation program may translate a parameter (e.g., text, data, etc.) to be visually output so that the parameter can be output via the audio output device 112.

The image acquisition probe 114 may obtain desired information under the control of the controller 102 and transmit this information to the controller 102 where it may be processed. The image acquisition probe 114 may include one or more transducer arrays, etc. For example, the present system may include a transducer such as, for example, a C5-1 transducer by Philips®.

The image acquisition control (IAC) device 116 may be controlled by the controller 102 and may include stabilization control devices (e.g., array stabilizers, etc.) which may control the position of the image acquisition probe (IAD) 114. For example, the IAC device 116 may include one or more devices to control the yaw, pitch, and/or roll of, for example, one or more transducer arrays relative to a handle, etc. Accordingly, the IAC device may control the position of the one or more transducer arrays about an x, y, or z axis and/or reduce undesired harmonics, vibration, etc. Further, the IAC device 116 may include a counter balance, a motor, a control system, etc., to control vibration, etc., of the one or more transducer arrays.

The user interface (UI) or user input device 118 may receive user inputs and transmit these inputs to, for example, the controller 102. The user input device 118 may include any suitable input device which can receive a user input, such as, a keyboard, a mouse, a touch pad, a track ball, a pointer, a digitizer, a touch screen, a finger-print reader, etc. Further, the user input device may include a biometric reader for inputting biometric information such as, for example, the fingerprint reader, an iris reader, etc.

The network 120 may include one or more of a local area network (LAN), a wide area network (WAN), the Internet, an intranet, a proprietary network, a system bus, and/or other transmission devices (active and/or passive) which may transmit information between various devices of the image-capturing system 100. The network 120 may operate using any suitable transmission scheme.

The remote storage device 122 may include any suitable memory device which can store information as required by the image-capturing system 100. Accordingly, the remote storage device 122 may include memory devices such as those described with reference to the memory 104. Further, the remote storage device may include a redundant array of independent disks (RAID) and/or other storage configurations. Moreover, the remote storage device 122 may include, for example, a storage area network (SAN). The remote storage device 122 may transmit/receive information to/from the controller 102 via the network 120 and/or the modem 108.

Figure 1B:
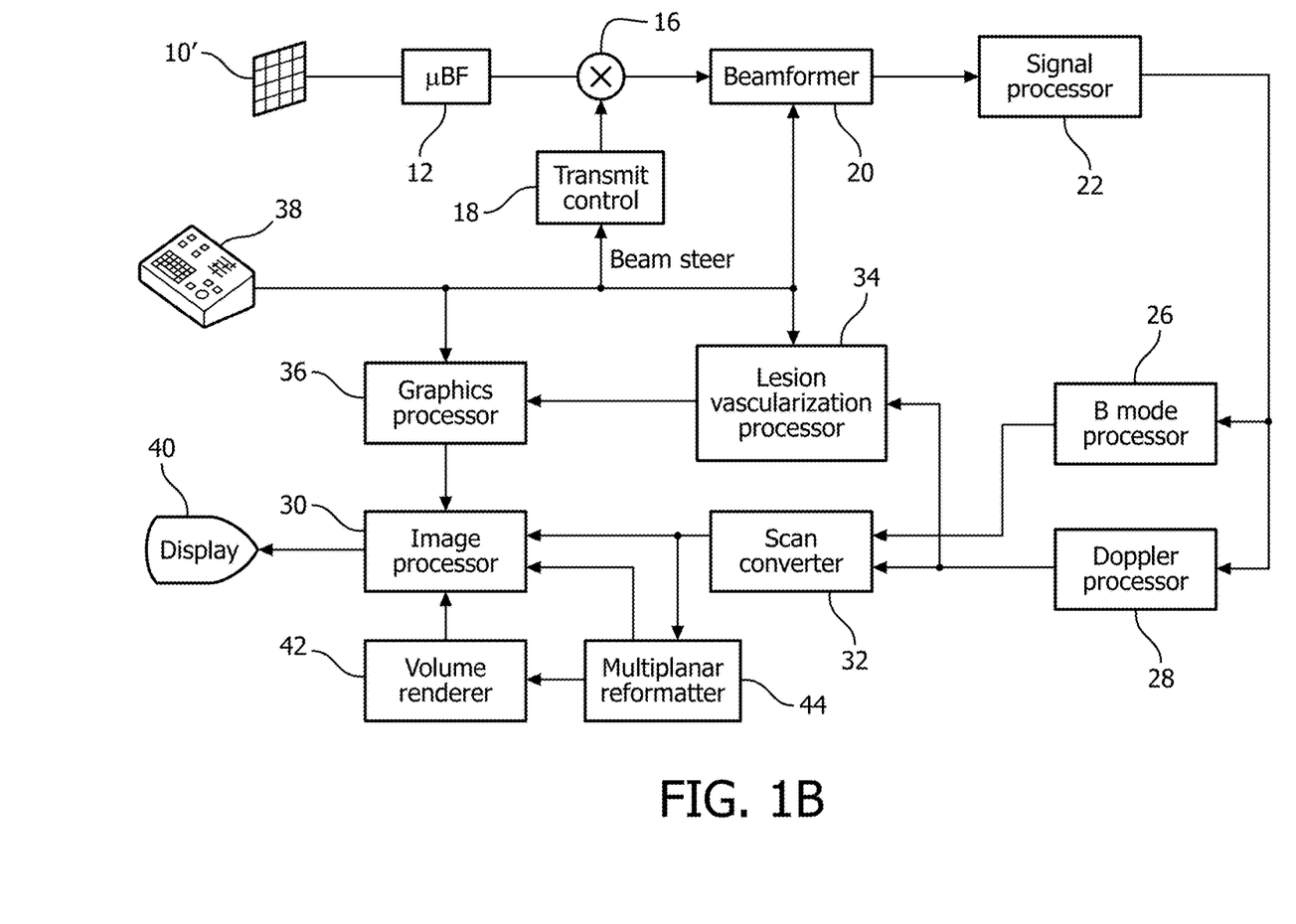
FIG. 1B is a schematic view of an embodiment of an ultrasound imaging system according to the present system.

Referring to FIG. 1B, an ultrasound imaging system constructed in accordance with the principles of the present invention is shown in block diagram form. In the ultrasonic diagnostic imaging system of FIG. 1B, a transducer array 10' is provided in an ultrasound probe 10 for transmitting ultrasonic waves and receiving echo information. The transducer array 10' is preferably a two dimensional array of transducer elements capable of scanning in three dimensions, for instance, in both elevation and azimuth about the location of the mitral valve, for 3D imaging. The transducer array is coupled to a microbeamformer 12 in the probe which controls transmission and reception of signals by the array elements. The microbeamformer is coupled by the probe cable to a transmit/receive (T/R) switch 16 which switches between transmission and reception and protects the main beamformer 20 from high energy transmit signals. The transmission of ultrasonic beams from the transducer array 10 under control of the microbeamformer 12 is directed by the transmit controller 18 coupled to the T/R switch and the beamformer 20, which receives input from the user's operation of the user interface or control panel 38. One of the functions controlled by the transmit controller is the direction in which beams are steered. Beams may be steered straight ahead from (orthogonal to) the transducer array, or at different angles for a wider field of view. The partially beamformed signals produced by the microbeamformer 12 are coupled to a main beamformer 20 where partially beamformed signals from the individual patches of elements are combined into a fully beamformed signal.

The beamformed signals are coupled to a signal processor 22. The signal processor 22 can process the received echo signals in various ways, such as bandpass filtering, decimation, I and Q component separation, and harmonic signal separation. The signal processor may also perform additional signal enhancement such as speckle reduction, signal compounding, and noise elimination. The processed signals are coupled to a B mode processor 26 and a Doppler processor 28. The B mode processor 26 employs amplitude detection for the imaging of structures in the body such as a tumor. The Doppler processor 28 processes temporally distinct signals from tissue and blood flow for the detection of the motion of substances such as the flow of blood cells in the image field. The structural and motion signals produced by the B mode and Doppler processors are coupled to a scan converter 32 and a multiplanar reformatter 44. The scan converter arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field corresponding with their Doppler-estimated velocities to produce a color Doppler image which depicts the motion of tissue and blood flow in the image field. The multiplanar reformatter can convert echoes which are received from points in a common plane in a volumetric region of the body into an ultrasonic image of that plane, as described in U.S. Pat. No. 6,443,896 (Detmer). A volume renderer 42 converts the echo signals of a 3D data set into a projected 3D image as viewed from a given reference point, e.g., as described in U.S. Pat. No. 6,530,885 (Entrekin et al.) The 2D or 3D images are coupled from the scan converter 32, multiplanar reformatter 44, and volume renderer 42 to an image processor 30 for further enhancement, buffering and temporary storage for display on an image display 40.

In accordance with the principles of the present invention, blood flow velocity values produced by the Doppler processor 28 are coupled to a lesion vascularization processor 34. The lesion vascularization processor operates as described below to produce a measure of the blood flow in or around a tumor being imaged by the system. The lesion vascularization processor may receive input from the user control panel 38, such as an initial estimate of the location of the tumor. Output data from the lesion vascularization processor is coupled to a graphics processor 36 for the reproduction of output data from the processor with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as a typed patient name. The user interface is also coupled to the transmit controller 18 to control the generation of ultrasound signals from the transducer array 10' and hence the images produced by the transducer array and the ultrasound system. The user interface is also coupled to the multiplanar reformatter 44 for selection and control of a display of multiple multiplanar reformatted (MPR) images which may be used to quantify blood flow in the MPR images of the tumor in accordance with the present invention as described below.

Figure 2A:
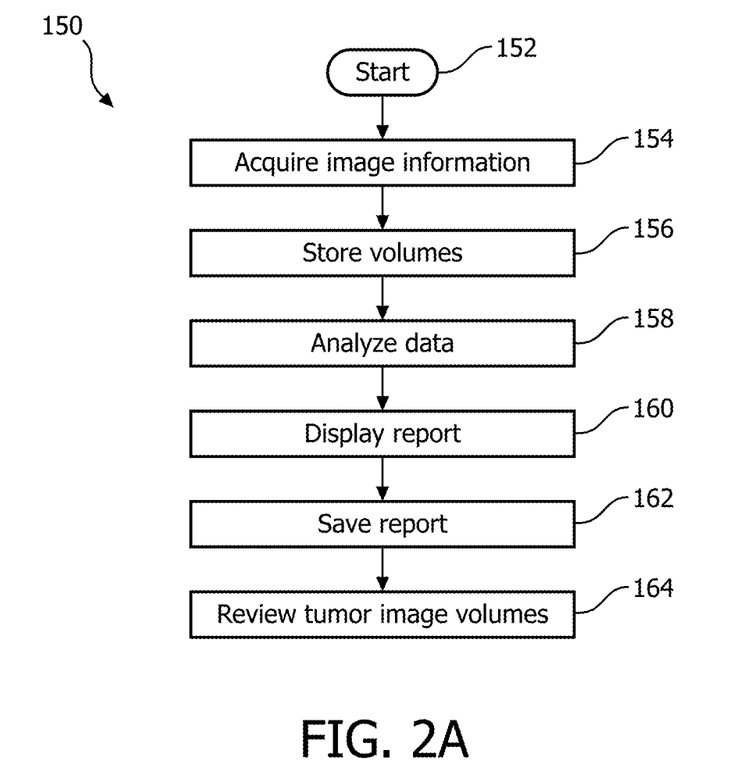
FIG. 2A is a flow chart illustrating a process performed according to an embodiment of the present system.

A process for capturing images and analyzing lesion volumes according to an embodiment of the present system will now be described. A flow chart corresponding to a process according to an embodiment of the present system is shown in FIG. 2A. A process 150 may be controlled by one more computers communicating directly and/or over a network. The process 150, as well as other processes according to the present methods, may be performed by execution of instructions embodied, e.g., on a computer readable medium (such as the memory 104) by a processor, such as the controller 102 or other similar component of a system described herein. The processor or controller 102 may be an application-specific or general-use integrated circuit(s). Further, the processor 102 may be a dedicated processor for performing in accordance with the present system or may be a general-purpose processor wherein only one of many functions operates for performing in accordance with the present system. The processor 102 may operate utilizing a program portion, multiple program segments, or may be a hardware device utilizing a dedicated or multi-purpose integrated circuit.

The process 150 may include one or more of the following steps, acts or operations. Further, one or more of these steps, acts, or operations may be combined and/or separated into sub-steps, sub-acts, or sub-operations, if desired. In act 152, a monitoring process such as, for example, a tumor monitoring automation process begins and proceeds to act 154.

In act 154, an image acquisition process is performed to acquire current image information. All necessary images should be acquired in act 154, however, act 154 may be repeated at other times to acquire other necessary images. After completing act 154, the process continues to act 156.

In act 156, the current image information (e.g., an image volume) may be stored in, for example, a local memory, a database, or other suitable memory. After completing act 156, the process may continue to act 158.

In act 158, the process may use an image processing routine to analyze/compare the current image information and the previous image information that was acquired previously (e.g., last month, last year, etc.). For example, according to the process, a user may measure lesions automatically by using an auto stack contour routing method (e.g., in QLAB™) or manually (e.g., by using a tracing function in QLAB™). The measurements, location, and/or contours of lesions may then be defined and/or recorded by generating a wire frame or mesh of the volume and assigning, for example, x, y, and/or z coordinates to user-defined points of interest (e.g., blood vessels). The x, y, and/or z coordinates of edges, contours, or user defined points of interest may be location information associated with the acquired image. This information may then be stored in a database or other suitable area for later use.

This information may then be used at a later time, such as, for example, when conducting a follow up imaging technique. For example when a patient has a successive tumor monitoring examination in which current image information is acquired, the image information acquired in one or more previous examinations, may then be retrieved or downloaded from the memory 104 or storage 122, and analyzed using any suitable image processing application, such as, for example, QLAB™, which may determine certain imaging parameters such as depth, focal zone location compression, contours, and/or x, y, and z coordinates, velocity information from Doppler techniques, echo intensity. One or more of such imaging parameters may be matched in a current examination to similar imaging parameters used in one or more previous tumor monitoring exams. This process may be performed by a user or by the system automatically. Accordingly, the system may access image parameter information to obtain information related to image parameters used in one or more previous tumor monitoring exams. An auto stack contours method (e.g., in QLAB™) may be applied to define tumor volumes across multiple images acquired in different planes in the same monitoring exam.

In accordance with an embodiment of the invention, location information such as, for example, x, y, and/or z coordinates of certain locations (e.g., corresponding with, for example, lesions, blood vessels, etc.) of image information corresponding with the previous examination, may be compared with corresponding information of image information associated with the current examination. For example, the wire frame of the volume from the previous examination may be embedded in the visualized volume of the current examination or vice versa. This may aid the operator in making consistent measurements across time, and increase confidence in the evaluation. An auto correlation and/or superimposition of additional image information may as also be performed.

After act 158, the process may continue to act 160.

In act 160, the process may display a corresponding report for a user's convenience. When the report is displayed, a user may enter additional text and/or annotations as necessary.

According to the present system, the system may extrapolate numeric values for the current and/or previous measurements in any position defined. The corresponding measurements may then be stored in the x, y, and/or z format during the analysis of the auto stack contours. Further, a "manual override" option may be provided for the user to enter information corresponding to a lesion such as, for example, lesion definition, lesion identification, etc., at any time.

After completing act 160, the process may continue to act 162.

In act 162, the process may generate a report and/or save the image information and any corresponding information (e.g., patient and probe orientation markers, lesion locations, lesion definitions, user information, date information, patient information, etc.) for later use and/or analysis, in any suitable location such as, for example, a database, etc.

After completing act 162, the process may continue to act 164.

In act 164, a physician or other user may further analyze the acquired images using a suitable image processing program such as, for example QLAB™. The physician may retrieve and display two or more acquired tumor volume images. The images may have been acquired at different points in time of the same tumor. The physician may use the image processing program to render a surface or a wire frame to the tumor volumes if such renderings were not already generated and saved in a suitable location. The rendering may also include demarcation of blood vessels in the tumor volume or proximate to the tumor volume. This may allow the physician to view the effect tumor treatment has on the vascularization of the tumor. The physician may view the volumes side-by-side. However, it may be advantageous to overlay the tumor volume images, rendered surfaces, wire frames, or combinations thereof.

Figure 2B:
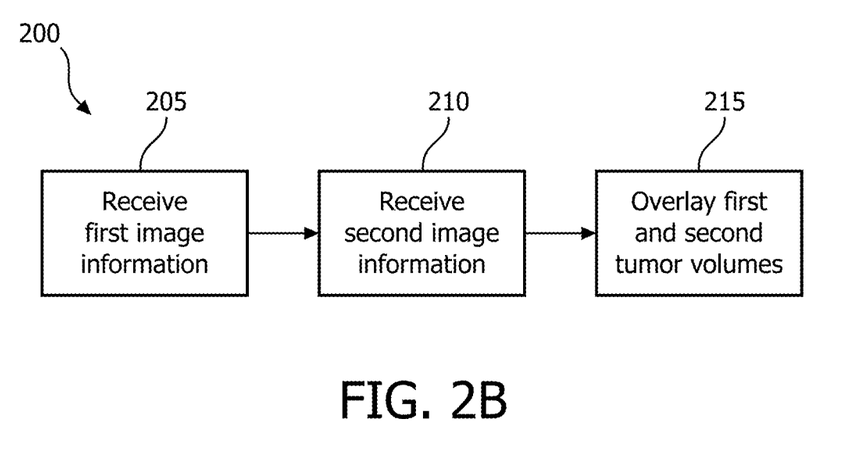
FIG. 2B is a flow chart illustrating another process performed according to an embodiment of the present system.

FIG. 2B illustrates a flow chart of a process 200 of overlaying the tumor volume images according to an embodiment of the present system. The first image information is received at act 205, and the second image information is received at act 210. Although shown sequentially, the image information may be loaded in either order or in parallel. The images are then overlaid at act 215. Location information included in the image information may be used during act 215 to align certain locations that may be common between the two images such as blood vessels and/or operator-defined points of interest. The process 200 may be incorporated into the image processing program previously described or may be performed by a separate software program or processor. Optionally, the process illustrated in FIG. 2 may be performed at act 158 in FIG. 1. The physician may also be able to independently rotate the images to manually correct for differences in acquisition angles. The physician may be able to adjust the alpha blending of the images (i.e., the opacity of each image) to enhance comparison between volumes. The physician may then observe changes in tumor shape, volume, and vascularization over time.

The physician may use the suitable image processing program to quantify tumor volume, tumor surface area, and ratio calculated volumes or surface areas between images. For example, with the lesion vascularization processor 34, the image processing program may also calculate the number of pixels within the volume that have blood flow (the "vascular index") and/or the velocity of blood flow (the "flow index"). These measurements may be considered vascularization indicators. The presence of blood flow is determined from a shift in the wavelength of the reflected signal in reference to the transmitted signal due to the Doppler Effect. The magnitude of the shift allows determination of the direction and velocity of flow. The suitable image processing program may plot the calculated values from each image for the indicators over time so that the physician may view trends in these indicators over time. Trends may include, for example, rates of change in an indicator and total change over time.

The visual analysis by the physician and the quantitative values calculated for volume, surface area, and vascularization indicators may assist the physician in more accurately evaluating the efficacy of tumor treatment and plan future treatment. For example, by presenting side-by-side 3D views, taken at different times during a treatment, and that are enhanced with wire frames of the tumor, the present systems and methods can aid physicians in making consistent tumor measurements over time, thereby increasing confidence in the evaluation. Furthermore, the ability to view changes in vasculature over time may also assist physicians in determining which vessel branch is providing the blood supply to the affected tumor segment. The physician may then be able to provide more targeted drug delivery, which may be more effective. For example, a physician compare two wire frame frames and determine which segment(s) of the tumor are shrinking or growing. By correlating the vascularization information, the physician could also identify which vessel(s) are providing blood supply to the affected tumor segment and then alter treatment accordingly.

The ability to visualize and quantify changes in vasculature features in a lesion may become increasingly important as more treatments are developed that target vascular formation in tumors. For example, anti-angiogenic therapies may have early effects on the vasculature when effective before changes in tumor volume may be detected. Changes in certain vascular features may also be an indicator of tumor aggressiveness and patient prognosis in some cases.

Figure 3:
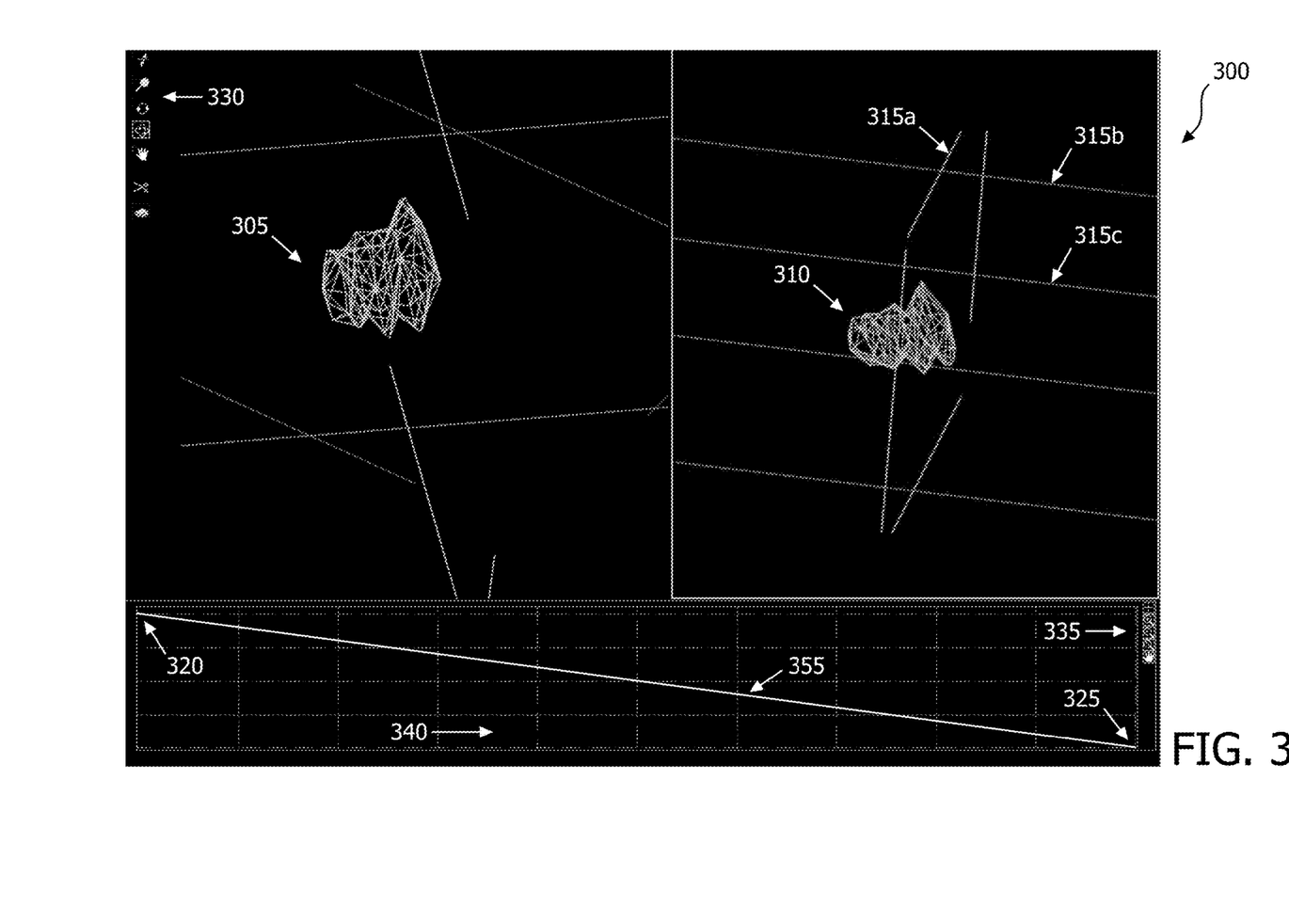
FIG. 3 is a screen shot illustrating an image display according to the present system.

A screen shot 300 illustrating an image display according to an embodiment of the present system is shown in FIG. 3. The screen shot 300 illustrates a screen which may be displayed using data which may correspond with a tumor. The screen shot 300 may also correspond with data that may be saved in a report. This data may include acquired image information, notes, annotations, measurements, day, date, time, patient's identification (ID), such as, for example, a number, a name, etc., medical professional data (e.g., sonographer's name, doctor's name, medical center's name, location, patient biometric information, etc.), viewing/editing history, change information, etc. The screen shot 300 may include one or more information areas in which user information, location (e.g., "Test Hospital"), day, date, time, type of exam (e.g., "TMR") and/or certain test parameters are displayed. (Not shown) An image viewing area may display one or more images such as, for example, images 305 and 310 which may have been acquired during a process (e.g., an image acquisition process, a download process, etc.) of an embodiment of present system. Image 305 may be an image of a wire frame rendered for a tumor volume measured at a time before a treatment was administered. Image 310 may be an image of a wire frame rendered for the tumor acquired at a time after or during the treatment. Reconstruction planes 315a-315c may be outlined in the images 305, 310 to assist in providing orientation to a user. A menu 230 may be provided to allow a user to easily access commonly used tools such as zoom, pan, and crop, for example. Below images 305, 310, a user may observe a chart of trend data 340 for the tumor. In the example illustrated in FIG. 3, tumor surface area has been calculated, but other indicators such as volume or vascularization may be calculated. The area calculated for the first time point 320 and the second time point 325 for the tumor may be plotted on the chart 340. In some embodiments, more time points may be calculated and plotted. A line of best fit 355 may be calculated for the plotted time points. A menu 335 may be provided to allow a user to easily access commonly used tools for manipulating the chart such a zoom and pan. Other tools may also be provided.

Although not shown, a small image (or likeness) of each of other images may be displayed in a smaller format (e.g., as icons) for a user's convenience in selecting images. This may be useful when all images corresponding with a certain examination or time periods of interest may not be displayed in the viewing area. Accordingly, a user may select one of the smaller images to view as an enlarged rendering of the selected image. Thus, by selecting an image (e.g., using a double click of a mouse, etc.), a user may cause the process to magnify the image. Further, a magnification view setting may be provided so that, selected views may be displayed in a window that may be larger than windows which display the other images (e.g., smaller views, icons, etc.). Further, as shown, when a point of interest such as a blood vessel is detected by the process, the blood vessel may be automatically assigned an identifier (ID) and other information. This information may be displayed in association with an image and may be included in the image information and saved for later use.

Figure 4:
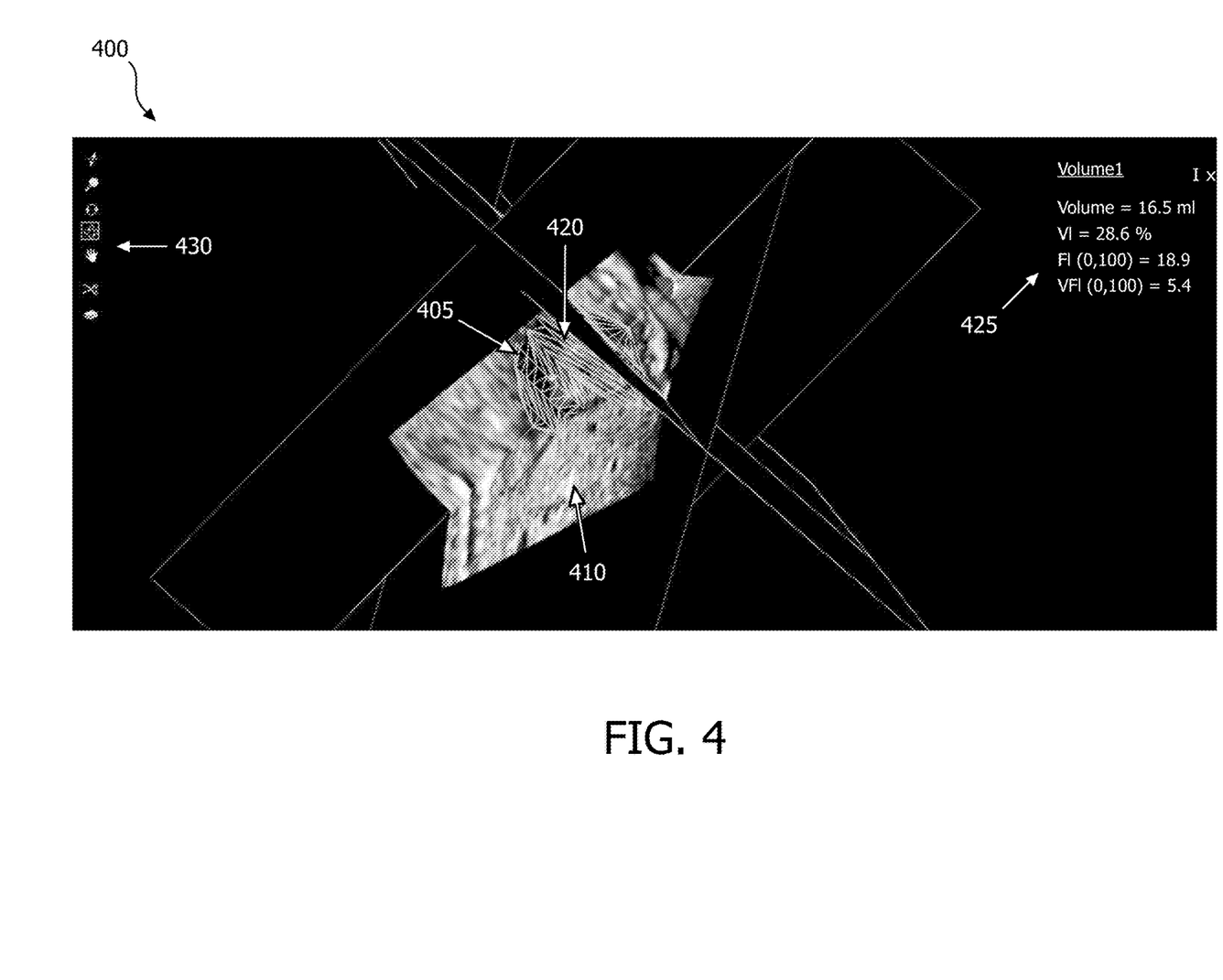
FIG. 4 is a screen shot illustrating another image display according to the present system.

A screen shot 400 illustrating a further image display according to an embodiment of the present system is shown in FIG. 4. The screen shot 400 illustrates image 410 which is a detailed image which corresponds with the wire frame 305 of FIG. 3. The user may use menu options 430 to generate a wire frame 405 or render a surface for the acquired volume image. A blood vessel 420 can be seen in image 410 within the tumor volume. A focal zone location indicator bar (not shown) may be displayed on the screen where a user may change it, e.g., via any user interface or control panel 38, such as a keyboard, mouse, or a pointer touching the screen in case of a touch sensitive screen. The user may also adjust the image intensity/contrast via selection. Of course, any other desired indictors or selection bars may be displayed as desired to provide further user control, such as a scroll/location bar so that the user may scroll the image. After inputting a user's selection, the image 310 and the corresponding image information such as, for example, annotations, caliper information, and/or other information may be saved for later use and review. The user may use menu options to calculate the volumes, vascularization index, and/or other parameters of the tumor volume images. A side panel 425 may be used to display the calculated parameters. In the example illustrated in FIG. 4, volume, vascular index (VI), flow index (FI), and vascular flow index (VFI) (in this embodiment, vascular flow index=vascular index X flow index) have been calculated using, e.g., the lesion vascularization processor 34 and are displayed. The user may then display a plot of the desired parameters over time as shown previously in FIG. 3.

Figure 5:
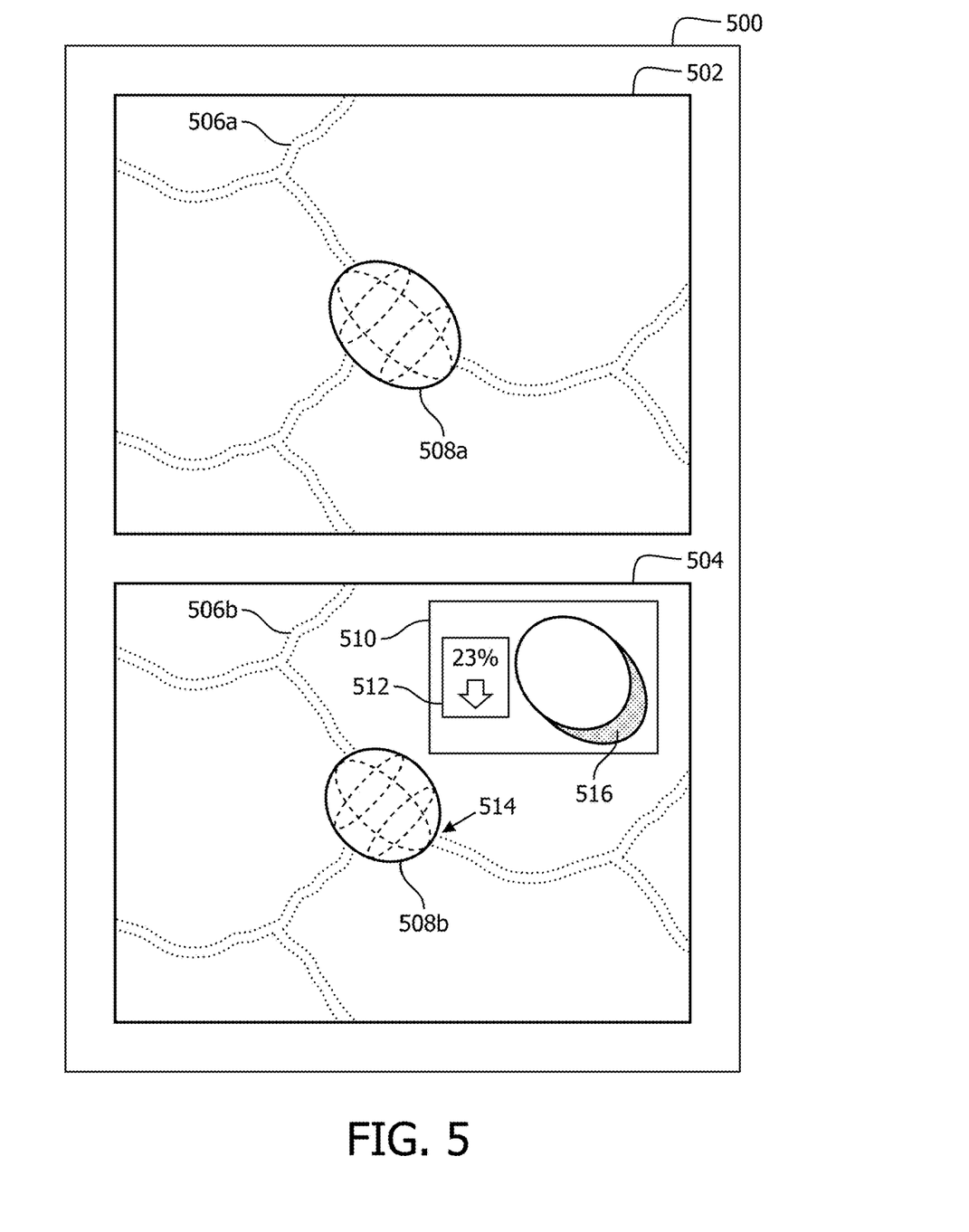
FIG. 5 is a screen shot illustrating a further image display according to the present system.

An example screen shot 500 illustrating yet another image display according to the present system is shown in FIG. 5. The screen shot 500 shows a first image 502 including a tumor volume 508a at a first time. Tumor vasculature 506a can also be identified in a B-mode image and flow of blood can be determined with Doppler imaging. A second image 504 is acquired at a second time and displayed with a wire frame representation of the tumor volume 508b. The respective tumor volumes at each time point can be compared. For example, the inset 510 illustrates a composite of the wire frame generated in image 502 overlaid with the wire frame generated in image 504. A similar approach can be used for image 305 and 310 above. Although two wire frames are shown, more than two volumes may be overlaid in some embodiments. In the inset or in another area of the display, a calculated volume difference 512 can also be shown to the physician to compare different tumor volumes, such as 508a and 508b. Furthermore, tumor vasculature 506a and 506b can also be analyzed to indicate where blood supply may be affected with respect to the tumor size change, e.g., as shown by the arrow 514. It is further envisioned that visual differences 516 in the tumor volumes can be displayed to the user for additional analysis of the shape and/or volume change of the tumor over time. Colors or other visual indicators could be used to identify differences. After inputting a user's selection, images 502 and 504 and any corresponding information such as, for example, annotations, caliper information, and/or other information may be saved for later use and review. Although not shown, the user may use menu options to calculate the volumes, vascularization index, and/or other parameters of the wire frames and plot the values similar to FIG. 3.

Although not shown, the screens 300, 400, and/or 500 may also illustrate user selections which may include, for example, icons or menu items which may be selected by the user to, for example, scan, file, print, transfer images (e.g., from one display to another), mute, transcribe, and/or use a headpiece, as desired. Further, one or more menus as is known in the art may be provided for a user's convenience. The displayed images and associated data may be saved at any time during the process shown in FIG. 1B or during subsequent physician analysis. However, a history mode may be activated to gather information indicative of when data may have been added and/or edited so that a user may refer back to original information and/or determine when and/or who made certain changes to information which may be saved in, for example, a generated report. Further, the changes may also be stored for later use.

Although the present system has been described with reference to a tumor ultrasound imaging system, it is also envisioned that the present system can be extended to other medical imaging systems where multiple images are obtained in a systematic manner at different points in time. Accordingly, the present system may be used to obtain and/or record image information related to renal, testicular, breast, ovarian, uterine, thyroid, hepatic, splenic, heart, arterial and vascular system, as well as other imaging applications. Further, the present system may also include or more programs which may be used with conventional imaging systems so that they may provide features and advantages of the present system.

Further, the present systems, apparatuses, and methods, may also be extended to any small parts imaging where the clear landmarks can be defined and reproduced. Further, the present methods may be embedded in a program code which may be applied to existing imaging systems such as, for example, ultrasonic imaging systems. Suitable ultrasonic imaging systems may include a Philips™ ultrasound system which may, for example, support a conventional broadband linear array transducer that may be suitable for small-parts imaging. Further, analysis techniques such as, for example, QLAB™ may be available on-cart with an imaging apparatus or as a post-processing program which may be run outside of an examination room. Further, multiple nodules, anatomical entities such as follicles, or other detectible objects, may be followed using the present system. Further, the method of the present systems may be applied to volumes acquired using transducers such as, for example, 2D array transducers, which may include, for example, X-Matrix™ or mechanical transducers.

Certain additional advantages and features of this invention may be apparent to those skilled in the art upon studying the disclosure, or may be experienced by persons employing the novel system and method of the present invention, chief of which is that a more reliable image acquisition system and method of operation thereof is provided. Another advantage of the present systems and method is that conventional medical image systems can be easily upgraded to incorporate the features and advantages of the present systems, devices, and methods.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A medical imaging system comprising code, which when executed, causes the system to:
receive at least two images of a region of interest, in which the at least two images include a first image obtained at a first time point and a second image obtained at a second time point;
receive a first plurality of coordinate points selected by a user in the first image and a second plurality of coordinate points selected by the user in the second image, the first and second pluralities of coordinate points corresponding to a target within the first and second image, respectively;
render a volumetric representation of the target based on the user-selected coordinate points within the respective one of the first image and the second image, wherein the user-selected coordinate points form a boundary or a contour of the volumetric representation; and
overlay at least a portion of the first image and the second image based on the volumetric representation of the target.

2. The system of claim 1, wherein the target comprises a lesion.

3. The system of claim 1, wherein the volumetric representation is a wireframe.

4. The system of claim 1, wherein the first plurality of coordinate points and the second plurality of coordinate points are selected by the user at different time points.

5. The system of claim 1, wherein the images are ultrasound images.

6. The system of claim 1, wherein the system is further configured to generate information corresponding to a change in the target based on the volumetric representations.

7. A method of image processing, the method comprising:
receiving at least two images of a region of interest, in which the at least two images include a first image obtained at a first time point and a second image obtained at a second time point;
receiving a first plurality of coordinate points selected by a user in the first image and a second plurality of coordinate points selected by the user in the second image, the first and second pluralities of coordinate points corresponding to a target within the first and second image, respectively;
rendering a volumetric representation of the target based on the user-selected coordinate points within the respective one of the first image and the second image, wherein the user-selected coordinate points form a boundary or a contour of the volumetric representation; and overlaying at least a portion of the first image and the second image based on the volumetric representation of the target.

8. The method of claim 7, wherein the first plurality of coordinate points and the second plurality of coordinate points correspond to contour information of a lesion, vascular locations, or both.

9. A non-transitory computer-readable medium storing instructions that, when executed by a computer, cause the computer to:
 receive at least two images of a region of interest, in which the at least two images include a first image obtained at a first time point and a second image obtained at a second time point;
 receive a first plurality of coordinate points selected by a user in the first image and a second plurality of coordinate points selected by the user in the second image, the first and second pluralities of coordinate points corresponding to a target within the first and second image, respectively;
 render a volumetric representation of the target based on the user-selected coordinate points within the respective one of the first image and the second image, wherein the user-selected coordinate points form a boundary or a contour of the volumetric representation; and
 overlay at least a portion of the first image and the second image based on the volumetric representation of the target.

10. The computer-readable medium of claim 9, wherein the first plurality of coordinate points and the second plurality of coordinate points correspond to a first vascular index and a second vascular index, respectively, the first and second vascular indices comprising a percentage of volume in the target that includes blood flow.

* * * * *